United States Patent [19]

Carson

[11] 4,214,114

[45] Jul. 22, 1980

[54] ISOPARAFFIN-OLEFIN ALKYLATION UTILIZING EVAPORATIVE COOLING IN A REACTOR-DEPROPANIZER

[75] Inventor: Don B. Carson, Mt. Prospect, Ill.

[73] Assignee: UOP Inc., Des Plaines, Ill.

[21] Appl. No.: 7,120

[22] Filed: Jan. 26, 1979

[51] Int. Cl.$^2$ ............................................. C07C 3/54
[52] U.S. Cl. .................................... 585/715; 585/719; 585/723; 585/730
[58] Field of Search ...................... 260/683.48, 683.59; 585/715, 719

[56] References Cited

U.S. PATENT DOCUMENTS

| | | | |
|---|---|---|---|
| 2,365,426 | 12/1944 | Molique | 260/683.59 |
| 2,768,987 | 10/1956 | Hart | 260/683.59 |
| 2,775,636 | 12/1956 | Rupp | 260/683.48 |
| 2,920,124 | 1/1960 | Stiles et al. | 260/683.59 |
| 3,170,002 | 2/1965 | Kelso | 260/683.59 |

Primary Examiner—George Crasanakis
Attorney, Agent, or Firm—James R. Hoatson, Jr.; Robert W. Welch; William H. Page, II

[57] ABSTRACT

A process for the acid-catalyzed alkylation of an isoparaffinic hydrocarbon with an olefinic hydrocarbon is disclosed. The alkylation is effected at alkylation reaction conditions resulting in an alkylation reaction mixture containing a vapor phase generated by the exothermic heat of reaction. The vapor phase so generated has a cooling effect permitting the alkylation reaction to be effected at lower temperatures more conducive to higher quality alkylation product.

12 Claims, 1 Drawing Figure

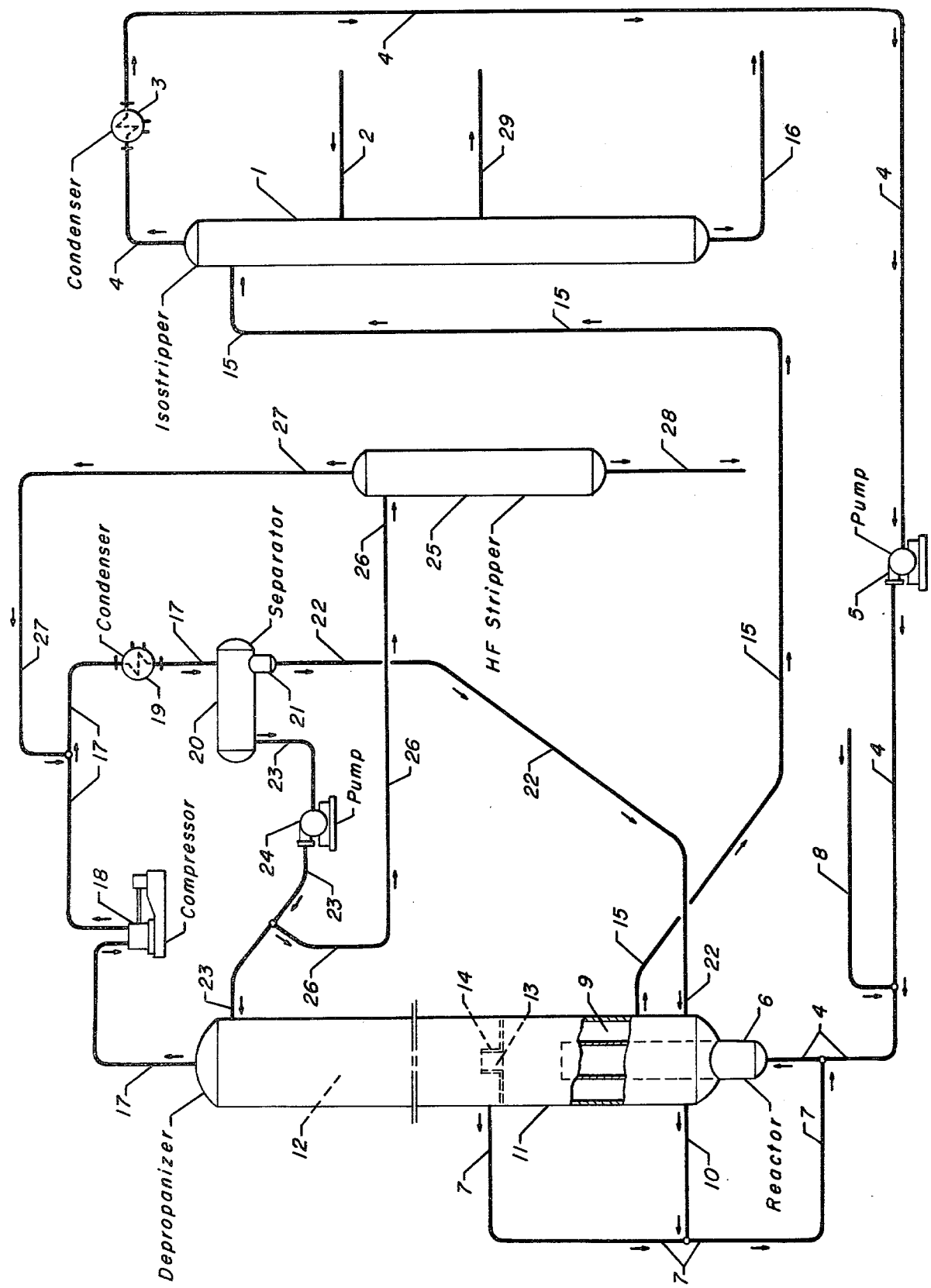

ISOPARAFFIN-OLEFIN ALKYLATION UTILIZING EVAPORATIVE COOLING IN A REACTOR-DEPROPANIZER

This invention relates to a process for the acid-catalyzed alkylation, and particularly the hydrofluoric acid-catalyzed alkylation, of an isoparaffinic hydrocarbon with an olefinic hydrocarbon to provide a normally liquid alkylate useful as a high octane motor fuel with enhanced anti-knock properties. The isoparaffinic hydrocarbon will typically contain from 4 to about 7 carbon atoms per molecule including, for example, isobutane, isopentane, neopentane, and the various isohexanes and isoheptanes. The olefinic hydrocarbon employed as an alkylating agent will generally contain from 3 to about 7 carbon atoms per molecule, for example, propene, n-butene, isobutene, and the isomeric pentenes, hexenes and heptenes, as well as mixtures thereof. In practice, the greater majority of hydrofluoric acid-catalyzed alkylation processes utilize isobutane as the isoparaffinic hydrocarbon and propene, butenes, or a mixture thereof as the olefinic hydrocarbon.

Since the advent of hydrofluoric acid-catalyzed alkylation, the process has experienced many changes and improvements with respect to unit design and operating techniques, and many innovations have been directed toward the effective cooling of the alkylation reaction mixture. This is mandatory in view of the exceptional evolution of heat which accompanies the alkylation reaction, and in further view of the fact that the lower the temperature in the range of from about 30° to about 100° F., the higher the quality of the alkylation reaction product. The present invention is directed not only to a more effective cooling of the alkylation reaction mixture, but also to a more effective utilization of the exothermic heat of reaction which is wasted in the more conventional alkylation processes.

It is an object of this invention to provide a method for controlling the exothermic heat of reaction in the acid-catalyzed alkylation of an isoparaffinic hydrocarbon with an olefinic hydrocarbon.

It is a further object to present a method for controlling said exothermic heat of reaction at a lower level than is achieved through the use of ambient temperature air or water as the cooling medium.

It is a still further object to afford a reduction in the capital investment and operating costs with respect to major vessels, equipment and off-site facilities associated with the acid-catalyzed alkylation of an isoparaffinic hydrocarbon with an olefinic hydrocarbon.

In one of its broad aspects, the present invention embodies a process for the alkylation of an isoparaffinic hydrocarbon with an olefinic hydrocarbon, which process comprises passing an alkylation reaction mixture comprising an isoparaffinic hydrocarbon, an olefinic hydrocarbon and an acid alkylation catalyst through an alkylation reaction zone at alkylation reaction conditions resulting in an alkylation reaction mixture containing a vapor phase generated by the exothermic heat of reaction and comprising unreacted isoparaffins and lower boiling n-paraffins, and a liquid phase comprising alkylate and acid alkylation catalyst; separating said liquid phase into an alkylate phase and an acid phase, recycling the acid phase to said alkylation reaction zone, and recovering the alkylate; withdrawing the vapor phase from said alkylation reaction mixture, and moving said vapor phase upwardly under the influence of said exothermic heat of reaction through a separation zone in open communication with said alkylation reaction zone; separating the isoparaffin as a bottom fraction of said vapor phase and recycling said fraction to said alkylation reaction zone; and separating any lower boiling n-paraffin as an overhead fraction.

One of the more specific embodiments of this invention concerns a process for the alkylation of isobutane with an olefinic hydrocarbon mixture of propylene and butylenes, which process comprises passing an alkylation reaction mixture comprising isobutane, said olefinic hydrocarbon mixture and a hydrofluoric acid catalyst through an alkylation reaction zone at alkylation reaction conditions resulting in an alkylation reaction mixture containing a vapor phase generated by the exothermic heat of reaction and comprising unreacted isobutane and a liquid phase comprising alkylate and acid alkylation catalyst, said alkylation reaction conditions including a pressure in the range of from about 35 to about 80 psig. as required to control the rate of vaporization, and the consequent cooling effect thereof, and maintain said alkylation reaction mixture at a temperature of from about 30° to about 60° F.; separating said liquid phase into an alkylate phase and an acid catalyst phase, recycling the acid catalyst phase to said alkylation reaction zone, and recovering the alkylate phase; withdrawing the vapor phase from said alkylation reaction mixture and moving said vapor phase upwardly under the influence of said exothermic heat of reaction through a separation zone in open communication with said alkylation reaction zone; separating isobutane as a bottoms fraction of said vapor phase, and recycling said fraction to said alkylation reaction zone; and separating the lower boiling n-paraffin as an overhead fraction of said vapor phase through a pressure control means responsive to the temperature of said alkylation reaction mixture.

Other objects and embodiments of this invention will become apparent in the following more detailed specification.

The concept of the present invention is particularly adapted for integration into an acid-catalyzed alkylation process for the production of normally liquid motor fuel alkylate comprising 7 or 8 carbon atoms per molecule. Therefore, in the interest of brevity, a further description of the process of this invention will be presented with reference to the alkylation of isobutane with an olefinic hydrocarbon mixture of propylene and butylenes. Since recycle isobutane, as well as external feedstocks including field butanes and olefinic hydrocarbons, say from a coking unit, will invariably contain some extraneous paraffinic material, such will appear in the reaction mixture. Hydrofluoric acid is utilized in an amount sufficient to provide an acid/hydrocarbon volume ratio in the alkylation reaction mixture of from about 0.5:1 to about 3:1. Generally, commercially available anhydrous hydrofluoric acid will be charged to the alkylation process as fresh catalyst. It is possible to use hydrofluoric acid containing as much as about 10% water. However, excessive dilution is undesirable since it tends to reduce the activity of the catalyst while introducing serious corrosion problems into the system.

To minimize the tendency of the olefinic component of the alkylation reaction mixture to undergo polymerization prior to alkylation, the molar ratio of isoparaffinic hydrocarbon to olefinic hydrocarbon is maintained at from about 1:1 to about 20:1, and preferably at from about 3:1 to about 15:1. Other alkylation reaction conditions include a temperature of from about 30° to about 100° F., and preferably from about 30° to about 60° F. Alkylation pressures are maintained sufficiently low to sustain the vapor phase generated in the alkylation reaction mixture by the exothermic heat of reaction as herein contemplated. The alkylation pressure will generally range from about 35 to about 150 psig., and preferably from about 35 to about 80 psig. Contact time in the alkylation reactor is conveniently expressed in terms of a space-time relationship which is defined as volumes of hydrofluoric acid in the reactor divided by the volume rate per minute of hydrocarbon reactants charged thereto. The space-time relationship will be less than about 5 minutes, and preferably less than about 2 minutes.

It is understood that the precise operating conditions employed for a given alkylation system is not limiting upon the present invention which directs itself to a unique technique for controlling and maintaining the temperature of the reaction mixture. Hydrocarbon alkylation reactions are highly exothermic, and every conceivable means is employed to maintain and control the reaction mixture temperature at that level which is consistent with the character of the reactant feed, other operating conditions and the desired quality of the ultimate alkylate product. Where the isoparaffin is isobutane, and the olefinic feed stream is a mixture of propylene and butylenes, the precise temperature at which the reaction mixture will be best maintained is principally dependent upon the propylene/butylene ratio as well as the 1-butene/2-butene/isobutene ratio.

A review of the prior art indicates that most commercial alkylation processes utilize refinery cooling water to absorb the exothermic heat of reaction by indirect heat exchange methods and maintain an acceptable alkylation reaction temperature. As a general rule, the quality of the alkylate product is a function of the cooling water inlet temperature. That is, alkylate quality improves with decreasing cooling water inlet temperatures. Obviously, the reaction mixture temperature cannot be less than the cooling water inlet temperature. At best, the minimum reaction temperature will approach the cooling water inlet temperature only within about 10° to about 20° F. In general, refinery cooling water is available at a temperature in excess of about 60° F., usually at a temperature of from about 80° to about 95° F. Since the temperature at which the alkylation reaction is effected is determined by the temperature of the effluent cooling water employed to absorb said heat of reaction, and since said alkylation reaction is preferably effected at a relatively low temperature not substantially in excess of that of the available refinery cooling water, the quantity of heat absorbed by a given volume of cooling water is limited to that which is absorbed over a relatively small temperature rise. Thus, extremely large volumes of cooling water are required in order to maintain the alkylation reaction mixture at the lowest possible temperature.

Aside from the more obvious advantages derived from the practice of this invention, the aforesaid prior art cooling deficiencies are substantially obviated. Thus, the temperature of the alkylation reaction mixture is minimized by a direct heat exchange effected between the reaction mixture and the vapors generated therein by the exothermic heat of reaction as the reaction progresses. Pursuant to the present invention, the vapors generated by the exothermic heat of reaction—which in a preferred embodiment are essentially isobutane vapors—are admitted to a depropanizer wherein the exothermic heat of reaction is further utilized not only to separate propane from the reaction mixture, but also to separate unreacted isobutane and generate a substantial if not major portion of the isobutane recycled to the alkylation reactor as is the general practice.

The further description of the process of this invention is present with reference to the attached drawing. In the drawing, the process is presented by way of a simplified flow diagram in which details such as pumps, instrumentation and other controls, quench systems, heat-exchange and heat-recovery circuits, valving, start-up lines and similar hardware have been eliminated as nonessential to an understanding of the techniques involved. Utilization of such miscellaneous appurtenances, to modify the process as illustrated, will become evident to those possessing the requisite skill in the art of petroleum refining technology.

Referring then to the drawing, field butanes are charged to an isostripper 1 through line 2 from an external source, not shown, isobutane being a major component of refinery-available field butanes recovered from other various refining processes. A higher boiling n-butane fraction is separated in the isostripper and discharged through line 29, and an isobutane fraction is recovered through an overhead condenser 3 contained in line 4. The isobutane is passed by way of line 4 and by means of a pump 5 to an alkylation reactor 6. The isobutane is charged to said alkylation reactor in admixture with isobutane recycled to said reactor by way of line 7 and line 4, and in further admixture with an olefinic hydrocarbon feedstock introduced to the alkylation process through line 8. The hydrofluoric acid catalyst component of the alkylation reaction mixture is primarily derived from an annular space 9 which serves as a hydrofluoric acid settler, and said acid is recycled through line 10 and charged to the alkylation reactor 6 admixed with the isobutane recycled through line 7.

The alkylation reactor 6 is shown in the drawing as an open-ended reactor extending into the bottom of a shell 11 which is common to said reactor and a depropanizer 12, said reactor being in open communication with said depropanizer through a riser 13 in a trap-out plate 14.

In illustration of one preferred embodiment of this invention, an olefinic hydrocarbon feedstock containing propylene and various butylenes and amylenes is charged to the alkylation reactor 6 at a rate of about 220 pound moles/hour of contained olefins, while the isobutane, including that recovered from field butanes and isobutane recycled to said reactor by way of line 7, is charged to said reactor at a rate of about 2900 pound moles/hour. The hydrofluoric acid catalyst is charged to the reactor at a rate of about 20,400 pound moles/hour, said hydrofluoric acid being inclusive of hydrofluoric acid recycled from said annular space 9 as well as hydrofluoric acid recovered and recycled from a hydrofluoric acid accumulator 21 as hereinafter described. The resulting reaction mixture charged to said alkylation reactor 6 will effect an exothermic heat of reaction in the order of about 6.65 million btu/hr.

The alkylation reaction mixture is processed upwardly through the alkylation reactor 6 at alkylation reaction conditions conducive to the vaporization of the isobutane and lower boiling components thereof. The vaporization process imparts a desired turbulence to the alkylation reaction mixture, but more importantly, said process provides an evaporative cooling effect sufficient to maintain the alkylation reaction mixture at a temperature of less than about 100° F., or at a temperature in the preferred range of from about 30° to about 60° F.

In the further illustration of one preferred embodiment of this invention, the isobutane/olefinic hydrocarbon mole ratio in said alkylation reaction mixture is maintained at about 13:1, and the hydrofluoric acid/hydrocarbon volumetric ratio at about 1.53:1. The alkylation reactor 6 is maintained at a pressure of from about 35 to about 80 psig., with the reaction mixture being maintained at a temperature of about 60° F. As heretofore mentioned, the alkylation reaction herein contemplated is a highly exothermic reaction, and the heat of reaction must be tempered with suitable cooling means. As generally practiced, the alkylation process is designed to maintain the alkylation reactor effluent at a temperature close to that of the available cooling medium. Typically, the alkylation reaction will be effected at a temperature of from about 80° to about 100° F. in an alkylation reaction zone designed to function as an indirect heat exchanger, and the cooling medium, usually water, is circulated through the reaction zone in indirect heat exchange relationship with the reaction mixture contained therein. Alternatively, copious quantities of the hydrofluoric acid catalyst can be cooled below the desired reaction temperature via indirect heat exchange with cooling water, and then admixed with the paraffinic and olefinic hydrocarbon reactants in an alkylation reaction zone such that the heat of reaction is absorbed as sensible heat in the acid phase of the reaction mixture. In accordance with the preferred embodiment illustrated herein, the aforementioned exothermic heat of reaction of about 6.65 million btu/hr is countered by the vaporization of about 750 pound moles of isobutane/hour in said alkylation reaction mixture, the required heat of vaporization being substantially equivalent to said exothermic heat of reaction. The vaporization rate, and thus the evaporative cooling, is pressure controlled at a pressure of from about 35 to about 80 psig., for example, by operating the compressor 18 responsive to the temperature of the alkylation reactor effluent.

In any case, the liquid phases of the alkylation reactor effluent are overflowed into the annular space 9 between the shell 11 and the alkylation reactor 6, said annular space serving as a hydrofluoric acid settler as heretofore mentioned. The lower hydrofluoric acid phase which settles out in said annular space is withdrawn through line 10 and recycled to the alkylation reactor 6 as heretofore described. The upper hydrocarbon phase is drawn off through line 15 and transferred to the isostripper 1 wherein unreacted isobutane is separated and recycled to the alkylation reactor 6 through a condenser 3 by way of line 4. The alkylate product is recovered from said isostripper as a bottoms fraction through line 16.

The vapor phase of the alkylation reaction mixture, generated by the exothermic heat of reaction, continues upwardly under the influence of said heat of reaction and passes through a riser 13 in a trap-out plate 14 into the depropanizer 12. The isobutane fraction of said vapor phase is condensed in said depropanizer and collected in said trap-out plate 14 for recycle to the alkylation reactor 6 as heretofore described.

A propane-rich depropanizer overhead is recovered through line 17 and passed through a compressor 18 and a condenser 19 to a separator 20. In the separator, a hydrofluoric acid phase is separated and settles into an accumulator 21 from which it is recovered and recycled via line 22 to the aforesaid annular space 9 and combined with the hydrofluoric acid phase contained therein. The propane-rich condensate recovered in said separator 20 is recycled through line 23 by means of pump 24 to said depropanizer 12 to provide reflux conditions therein. A portion of the propane-rich condensate is diverted from line 23 and passed to a hydrofluoric acid stripper 25 through line 26. The hydrofluoric acid recovered overhead from said stripper is recycled to the separator 20 through lines 27 and 17 and the aforesaid condenser 19. A propane-rich product is recovered from the hydrofluoric acid stripper through line 28.

I claim as my invention:
1. An alkylation process which comprises:
   (a) introducing upwardly into an alkylation reaction zone maintained under alkylation reaction conditions including liquid phase alkylation, an alkylation reaction mixture comprising an isoparaffinic hydrocarbon, a lower boiling normal paraffinic hydrocarbon, an olefinic hydrocarbon and an acid alkylation catalyst;
   (b) reacting the olefinic hydrocarbon with a portion of said isoparaffinic hydrocarbon in said zone;
   (c) vaporizing from the liquid reaction mixture of said zone by the exothermic heat of reaction, a sufficient quantity of unreacted isoparaffinic and normal paraffinic hydrocarbons to provide an adequate evaporative cooling effect to maintain the reaction mixture in said zone at a temperature of from about 30° to about 100° F. without extraneous cooling;
   (d) passing the resultant vapors from said liquid phase in the reaction zone upwardly into a separation zone in open communication with said reaction zone;
   (e) separating normal paraffinic hydrocarbon vapor from unreacted isoparaffinic hydrocarbon in said separation zone and returning said unreacted isoparaffinic hydrocarbon as a liquid to the alkylation reaction zone; and
   (f) separating the liquid phase from the alkylation reaction zone into an alkylate phase and a catalyst phase, recycling the separated catalytic phase to said alkylation reaction zone and recovering the alkylate product from said alkylate phase.

2. The process of claim 1 further characterized in that said acid alkylation catalyst is a hydrofluoric acid alkylation catalyst.

3. The process of claim 1 further characterized in that said acid alkylation catalyst is a sulfuric acid alkylation catalyst.

4. The process of claim 1 further characterized in that said isoparaffinic hydrocarbon contains from about 4 to about 7 carbon atoms.

5. The process of claim 1 further characterized in that said isoparaffinic hydrocarbon is isobutane.

6. The process of claim 1 further characterized in that said olefinic hydrocarbon contains from about 3 to about 7 carbon atoms.

7. The process of claim 1 further characterized in that said olefinic hydrocarbon is a mixture of propylene and butylenes.

8. The process of claim 1 further characterized in that said alkylation reaction conditions include an isoparaffin/olefin mole ratio of from about 1:1 to about 20:1.

9. The process of claim 1 further characterized in that said alkylation reaction conditions include an isoparaffin/olefin mole ratio of from about 3:1 to about 15:1.

10. The process of claim 1 further characterized in that said alkylation reaction conditions include a pressure in the range of from about 35 to about 150 psig. as required to control the rate of vaporization and the consequent cooling effect thereof and maintain said alkylation reaction mixture at a temperature of from about 30° to about 100° F.

11. The process of claim 1 further characterized in that said alkylation reaction conditions include a pressure in the range of from about 35 to about 80 psig. as required to control the rate of vaporization and the consequent cooling effect thereof and maintain said alkylation reaction mixture at a temperature of from about 30° to about 60° F.

12. The process of claim 1 further characterized in that the heat of vaporization of the hydrocarbons vaporized in said reaction zone is substantially equivalent to the exothermic heat of reaction in the reaction zone.

* * * * *